United States Patent [19]

Raschack et al.

[11] Patent Number: 4,596,820

[45] Date of Patent: Jun. 24, 1986

[54] 1,7-DIPHENYL-3-METHYLAZA-7-CYANO-8-METHYLNONANE FOR USE IN THE TREATMENT OF DISEASES

[75] Inventors: Manfred Raschack, Weisenheim am Sand; Horst Kreiskott, Wachenheim; Werner Seitz, Plankstadt, all of Fed. Rep. of Germany

[73] Assignee: BASF Aktiengesellschaft, Fed. Rep. of Germany

[21] Appl. No.: 680,059

[22] Filed: Dec. 10, 1984

[30] Foreign Application Priority Data

Dec. 10, 1983 [DE] Fed. Rep. of Germany ....... 3344755

[51] Int. Cl.[4] .................. A61K 31/275; C07C 121/78
[52] U.S. Cl. .................................... 514/523; 558/408
[58] Field of Search .................. 260/465 E; 424/304; 514/523

[56] References Cited

U.S. PATENT DOCUMENTS

| 3,261,859 | 7/1966 | Dengel | 260/465 E |
| 4,305,887 | 12/1981 | Herrling | 260/465 E |
| 4,418,017 | 11/1983 | Seitz et al. | 260/465 E |
| 4,438,131 | 3/1984 | Ehrmann et al. | 260/465 E X |

FOREIGN PATENT DOCUMENTS 1367677 9/1974 United Kingdom .
1377209 12/1974 United Kingdom .

OTHER PUBLICATIONS

Rote Liste 1983.
Mannhold et al, Arzneim–Forch./Drug. Res. 31 (I), No. 5 (1981) pp. 773–780.

*Primary Examiner*—Dolph H. Torrence
*Attorney, Agent, or Firm*—Keil & Weinkauf

[57] ABSTRACT

1,7-diphenyl-3-methylaza-7-cyano-8-methylnonane and its antipodes and salts are used for the treatment of diseases.

9 Claims, No Drawings

1,7-DIPHENYL-3-METHYLAZA-7-CYANO-8-METHYLNONANE FOR USE IN THE TREATMENT OF DISEASES

Phenylacetonitriles have been disclosed (German Pat. No. 1,154,810). For example, verapamil and gallopamil are used as antiarrhythmic agents or coronary agents (cf. *Rote Liste* 1983).

It has also been stated that exchange of the methoxy groups on the phenyl nuclei in these compounds for hydrogen atoms results in compounds which cannot be used (*Arzneim.-Forsch.* 31, (1981), 773).

We have found that 1,7-diphenyl-3-methylaza-7-cyano-8-methylnonane and its salts with physiologically tolerated acids are very useful for the protective treatment of hypoxic tissue damage.

1,7-Diphenyl-3-methylaza-7-cyano-8-methylnonane can also be used in the form of its optical antipodes, which are obtained by reacting the racemate with chiral acids, separating the resulting mixture of diastereomeric salts, liberating the bases from the salts thus obtained, and, if desired, converting these bases to their salts with physiologically tolerated acids.

Examples of chiral acids are the optically active forms of camphor-10-sulfonic acid, alpha-bromocamphor-pisulfonic acid, camphoric acid, menthoxyacetic acid, tartaric acid, mandelic acid, alpha-methoxy-alpha-trifluoromethyl phenylacetic acid and O,O-diacetyl-, O,O-dibenzoyl- and O,O-di-4-toluoyltartaric acid.

The diasteriomeric salts can be separated in a conventional manner, for example by fractional crystallization or column chromatography.

Separation of the racemates can also be carried out by column chromatography. Examples of suitable chiral stationary phases are optically active polymethyl acrylates, 2,4-dinitrobenzoylphenylglycine bonded to aminopropyl-silica gel, acetylated and/or benzoylated cross-linked cellulose, cellulose tribenzyl ether and/or cellulose phenylcarbamate. In this case, the pure antipodes are obtained directly by passing the racemate over a column containing one of the stated stationary phases.

The specific examples of physiologically tolerated acids which are suitable for salt formation with 1,7-diphenyl-3-methylaza-7-cyano-8-methylnonane and its antipodes are sulfuric acid, phosphoric acid, tartaric acid, acetic acid, succinic acid, lactic acid, citric acid, amidosulfonic acid and, in particular, hydrochloric acid.

1,7-Diphenyl-3-methylaza-8-methylnonane is prepared in a conventional manner, for example by reacting alpha-isopropylbenzyl cyanide with N-(3-chloropropyl)-N-methylphenethylamine.

As stated above, 1,7-diphenyl-3-methylaza-8-methylnonane is very useful for the protective treatment of hypoxic tissue damage. Such damage occurs rapidly in the case of oxygen deficiency, in particular in the heart, in the brain and in the kidney during conditions of ischemia or shock, and often causes permanent defects or even death. Hypoxic damage is also possible during reduction of the blood supply to organs, which has to be undertaken, for example, because of operative procedures.

The good action of 1,7-diphenyl-3-methylaza-8-methyl-8-octylnonane (referred to as A below) can be demonstrated by the following experiments:

Male Wistar rats weighing 250–300 g were anesthetized intraperitoneally with thiobutabarbital (100 mg/kg of body weight) and then subjected to standardized ventilation with an oxygen-deficient mixture (2% of $O_2$ and 98% of $N_2$) for 7 minutes. Using the freeze-stop technique, the apex of the heart was removed, mechanically comminuted and then digested with the addition of 0.6N perchloric acid. After centrifuging, creatine phosphate (according to Bergmeyer, H. U., Methoden der enzymatischen Analyse, Verlag Chemie, Weinheim, 2, (1974), 1825), adenosine triphosphate (according to Biochem. Biophys. Acta (Amst.) 1 (1947), 292) and glycogen (according to Biochem. J. 56 (1954), 1825) were determined in the supernatant liquid.

The test substances were administered to the conscious animals at various times before they were anesthetized and before the subsequent ventilation with an oxygen-deficient mixture. The percentage difference in the myocardial concentrations of adenosine triphosphate (ATP), creatine phosphate (CP) and glycogen in animals pretreated with the test substance compared with untreated hypoxic control animals was determined.

Table 1 shows that even the lowest dose tested, ie. 5 mg/kg of A administered orally, substantially inhibits the hypoxic reduction in the level of creatine phosphate, adenosine triphosphate and glycogen in the heart muscle. An increase in dose results in a greater protective effect.

TABLE 1

Myocardial protection 6 hours after oral administration of A to the rat

| Amount of A administered mg/kg | Percentage difference in the amount of | | |
|---|---|---|---|
| | CP | ATP | Glycogen |
| 5 | 29 | 24 | 10 |
| 10 | 47 | 37 | 27 |
| 20 | 80 | 63 | 50 |

Table 2 shows the long-term protective effect of A, this effect being clearly detectable for the parameters CP and ATP as soon as 2 hours after administration of the well tolerated dose of 20 mg/kg, and lasts for up to 24 hours.

TABLE 2

Cardioprotective long-term effect of A on the rat
Dose: 20 mg/kg, administered orally

| Hours after administration of the substance | Percentage difference in the amount of | | |
|---|---|---|---|
| | CP | ATP | Glycogen |
| 2 | 41 | 31 | −1 |
| 6 | 80 | 63 | 50 |
| 12 | 42 | 42 | 19 |
| 18 | 32 | 40 | 16 |
| 24 | 22 | 11 | 26 |

Table 3 demonstrates that the cardioprotective action of A is substantially superior to that of verapamil. In contrast to A, verapamil, when administered in the same dose or even in a dose which is 4 times higher, has no significant protective action against the hypoxia-induced reduction in the myocardial levels of CP, ATP and glycogen 6 hours after oral administration.

TABLE 3

Comparison of the myocardial protection obtained with A and verapamil 6 hours after oral administration to the rat

| Substance | Dose mg/kg | Percentage difference in the amount of CP | ATP | Glycogen |
|---|---|---|---|---|
| A | 20 | 80 | 63 | 50 |
| verapamil | 20 | −9 | 0 | 9 |
| " | 40 | 9 | 9 | −5 |
| " | 80 | 21 | 20 | 2 |

Table 4 compares the efficacy of the racemate and the optical isomers of A. When tested separately, both enantiomers exhibit a dose-dependent cardioprotective action. The effective dose of the levorotatory form is substantially lower than that of the dextrorotatory antipode. (−)A is about twice as effective as the racemate, while (+)A possesses about one fourth of the efficacy of the racemate.

TABLE 4

Myocardial protection in the rat 6 hours after oral administration. The ED 50% is the pretreatment dose of test substance which increases the ATP level by 50% compared with the hypoxic control group.

| Substance | ED 50% mg/kg | Relative activity |
|---|---|---|
| (±) A | 13.6 | 1 |
| (−) A | 6.6 | 2.06 |
| (+) A | 50.3 | 0.27 |

Surprisingly, we have furthermore found that A, even when administered orally in a dose of 20 mg/kg, which has a maximum cardioprotective effect in the rat, has no significant effect on the blood pressure (measured with piezo pulse recorders) and heart rate of spontaneously hypertensive rats (Table 5); the changes are not significant. Hence, A surprisingly possesses good cardioprotective properties (cf. Tables 2 to 4) in hemodynamically neutral doses. In contrast, similar doses of verapamil have the known effects on the heart and the circulation, eg. reduction in blood pressure and inhibition of AV conduction.

TABLE 5

Effect of A on blood pressure and heart rate of conscious spontaneously hypertensive rats
Dose: 20 mg/kg, administered orally

| | Initial value | 6 hours after administration of the substance | Change in % |
|---|---|---|---|
| Blood pressure | 229 | 217 | −5 |
| Heart rate | 398 | 378 | −5 |

Hence, the risk of provoking conduction disturbances is substantially lower in the case of A than for verapamil. The effect on the AV conduction was tested on a species suitable for this purpose, ie. the dog. Even 5 times the dose which, in the case of verapamil (0.4 mg/kg, administered intravenously), causes second degree AV blocks in all experimental animals and greatly prolongs the PQ interval has no adverse effect at all on the AV conduction in the case of A. Hence, taking into account the superior cardioprotective action, A has a substantially greater therapeutic index than verapamil.

The good toleration of A compared with verapamil can also be demonstrated in a further experiment: when administered intravenously in a dose of 0.2 mg/kg to anesthetized pigs, verapamil results in the expected pronounced increase in the PQ interval and reduction in the myocardial contractility (maximum systolic rate of increase in pressure in the left ventricle). In contrast, the injection of A in a dose which is 20 times higher (4 mg/kg, intravenously) does not result in any significant changes in these parameters.

It has also been possible to demonstrate a superior protective action, compared with verapamil, against cerebral hypoxia in the mouse. To test for tolerance to hypoxia, female mice (NMRI Ivanovas, weight 24–26 g) were introduced individually into glass tubes through which a gas mixture consisting of 96.5% of $N_2$ and 3.5% of $O_2$ flowed via a rotameter, at a rate of 4 liters/min. The time from the beginning of passage of the gas mixture until death occurred was measured. In contrast to the comparison compound verapamil, which is ineffective in this experiment, A and its antipodes (particularly (−)A) increase the number of experimental animals which survive after 3 minutes, this effect being dose-dependent. All control animals, like the animals pretreated with verapamil, were dead after 3 minutes.

TABLE 6

Tolerance of the mouse to hypoxia, test carried out 1 hour after oral administration of the test substances.
ED 50% means that, at the stated dose, 50% of the animals survived oxygen-deficient ventilation for 3 minutes.

| Substance | ED 50% mg/kg |
|---|---|
| A | 88 |
| (−) A | 48 |
| (+) A | 100 |

Hence, A exhibits great oral availability and a long duration of action. Moreover, it is particularly well tolerated and does not result in a reduction in the blood pressure. The selectivity of the organ-protecting action of A includes the advantage of greater therapeutic safety, since the substance can also be used without risk in patients with previously damaged AV conduction or labile blood pressure.

A and its antipodes are particularly useful for treatment of the following indications: Hypoxemic conditions of vital organs, such as heart, brain and kidney, as a result of circulatory disturbances or blood loss (hemorrhagic shock), hypobaric and functional hypoxic conditions (altitude sickness, epilepsy and cardiac arrhythmia), intoxication, traumatic organ damage, organ protection (for heart, brain and kidney operations) and in the case of transplantations.

The compound according to the invention, and its antipodes, can be administered in a conventional manner, orally or parenterally (intravenously, intramuscularly or intraperitoneally).

The dose depends on the age, condition and weight of the patient and on the route of administration. As a rule, the daily dose of active compound is from about 1 to 10 mg/kg of body weight in the case of oral administration, and from about 0.1 to 1 mg/kg of body weight in the case of parenteral administration.

The compound according to the invention, and its antipodes, may be employed in the conventional solid or liquid pharmaceutical forms, such as tablets, film tablets, capsules, powders, granules, coated tablets or solutions. These are prepared in a conventional manner, and to do so the active compounds can be mixed with the conventional pharmaceutical auxiliaries, such as tablet binders, fillers, preservatives, tablet disintegrators, flow regulators, plasticizers, wetting agents, dispersants, emulsifiers, solvents, retarding agents and/or antioxidants (cf. H. Sucker et al: *Pharmazeutische Technologie*, Thieme Verlag, Stuttgart, 1978). The formulations thus obtained normally contain from 0.1 to 99% by weight of the active compound.

The Examples which follow illustrate the invention.

EXAMPLE 1

(±)-1,7-Diphenyl-3-methylaza-7-cyano-8-methylnonane hydrochloride 15.9 g (0.1 mole) of alpha-isopropylbenzyl cyanide were dissolved in 20 ml of toluene in a 3-necked flask equipped with a stirrer, a dropping funnel and a reflux condenser, and 29.5 g of 85% pure technical-grade potassium hydroxide powder and 0.3 g of tetrabutylammonium iodide were added to this solution. The reaction mixture was heated to 80° C., while stirring vigorously, and a solution of 21.2 g (0.1 mole) of N-(3-chloropropyl)-N-methylphenethylamine in 20 ml of toluene was added dropwise, starting at this temperature, at a rate such that the reaction temperature did not exceed 85° C. When the addition was complete, stirring was continued for 3 hours at from 85° to 90° C. 100 ml of water and 100 ml of toluene were added to the cold reaction mixture, the toluene phase was separated off, washed several times with water and dried, and the solvent was stripped off to give 30 g of residue. This was dissolved in 200 ml of ethyl acetate, and ethanolic hydrochloric acid was then added. After 15 hours, 32 g (85%) of the hydrochloride of melting point 166°–168° C. were isolated.

EXAMPLE 2

(+)-1,7-Diphenyl-3-methylaza-7-cyano-8-methylnonane 40.4 g (0.12 mole) of racemic 1,7-diphenyl-3-methylaza-7-cyano-8-methylnonane and 48.5 g (0.12 mole) of (−)-O,O'-di-4-toluoyl-L-tartaric acid were dissolved in 400 ml of isopropanol, while heating. The crystals which were precipitated overnight were filtered off under suction and recrystallized twice from a 4:1 ethanol/water mixture. The angle of rotation found, ie. $[alpha]_D^{20} = -70.5$ (methanol, c=10 mg/ml), did not change when crystallization was repeated. The base liberated from the salt had an angle of rotation $[alpha]_D^{20}$ of +20.4° (benzene, c=10 mg/ml).

The base was dissolved in 100 ml of ethyl acetate, and ethanolic hydrochloric acid was added until the pH was 3. Crystallization from a 4:1 ethyl acetate/ethanol mixture and drying gave 15.6 g (70%) of the hydrochloride of melting point 184°–185° C. and $[alpha]_D^{20} = +11.3°$ (ethanol, c=10 mg/ml).

EXAMPLE 3

(−)-1,7-Diphenyl-3-methylaza-7-cyano-8-methylnonane

The mother liquor obtained in Example 2 after precipitation with (−)-O,O'-di-4-toluoyl-L-tartaric acid was evaporated down under reduced pressure, the residue was taken up in water, and the base was liberated from this by adding potassium carbonate. Extraction with n-hexane, drying over magnesium sulfate and removal of the solvent by distillation gave 20.4 g of an oil.

This oily residue and 24.2 g (0.06 mole) of (+)-O,O'-di-4-toluoyl-D-tartaric acid were dissolved in 200 ml of isopropanol, while heating. After 3 hours, the precipitated crystals were filtered off under suction and recrystallized twice from a 4:1 ethanol/water mixture. The angle of rotation of the salt, $[alpha]_D^{20} = +70.4°$ (methanol, c=10 mg/ml), did not change when crystallization was carried out once again. The base liberated from the salt had an angle of rotation $[alpha]_D^{20}$ of −20.4° (benzene, c=10 mg/ml).

The hydrochloride was obtained from the base as described in Example 2. The yield was 16.8 g (75%). Mp.=184°–185° C.; $[alpha]_D^{20} = -11.3°$ (ethanol, c=10 mg/ml).

EXAMPLE 4

Tablets having the following composition were prepared in a conventional manner on a tabletting machine:
40 mg of the substance of Example 1,
120 mg of corn starch,
13.5 mg of gelatine,
45 mg of lactose,
2.25 mg of Aerosil ® (chemically pure silica in submicroscopically fine dispersion) and
6.75 mg of potato starch (as a 6% strength paste).

EXAMPLE 5

Coated tablets having the following composition were prepared in a conventional manner:
20 mg of the substance of Example 3,
60 mg of core material and
60 mg of sugar-coating material.

The core material consisted of 9 parts of corn starch, 3 parts of lactose and 1 part of Luviskol ® VA 64 (60:40 vinylpyrrolidone/vinyl acetate copolymer, cf. *Pharm. Ind.* 1962, 586). The sugar-coating material consisted of 5 parts of sucrose, 2 parts of corn starch, 2 parts of calcium carbonate and 1 part of talc. The coated tablets prepared in this manner were then provided with a coating resistant to gastric juices.

EXAMPLE 6

10 g of the substance of Example 3 were dissolved in 5,000 ml of water with the addition of NaCl, and the solution was brought to pH 6.0 with 0.1N NaOH so that a blood-isotonic solution resulted. 5 ml portions of this solution were introduced into ampoules and then sterilized.

We claim:

1. (−)-1,7-Diphenyl-3-methylaza-7-cyano-8-methylnonane and its salts of physiologically tolerated acids.

2. (−)-1,7-Diphenyl-3-methylaza-7-cyano-8-methylnonane.

3. The hydrochloride of (−)-1,7-diphenyl-3-methylaza-7-cyano-8-methylnonane.

4. A therapeutic composition comprising a pharmaceutical excipient and an effective amount of (±)-1,7-diphenyl-3-methylaza-7-cyano-8-methylnonane or its salts of physiologically tolerated acids.

5. A therapeutic composition comprising a pharmaceutical excipient and an effective amount of (−)-1,7-diphenyl-3-methylaza-7-cyano-8-methylnonane or its salts of physiologically tolerated acids.

6. The composition of claim 6, wherein the active agent is the hydrochloride of (−)-1,7-diphenyl-3-methylaza-7-cyano-8-methylnonane.

7. The method of protectively treating hypoxic tissue damage in a patient suffering from ischemic and shock conditions, which comprises administering to the patient an effective amount of (±)-1,7-diphenyl-3-methylaza-7-cyano-8-methylnonane or its salts of physiologically tolerated acids.

8. The method of protectively treating hypoxic tissue damage in a patient suffering from ischemic and shock conditions, which comprises administering to the patent an effective amount of (—)-1,7-diphenyl-3-methylaza-7-cyano-8-methylnonane or its salts of physiologically tolerated acids.

9. The method of claim 5, wherein the active agent is the hydrochloride of (—)-1,7-diphenyl-3-methylaza-7-cyano-8-methylnonane.

* * * * *

UNITED STATES PATENT AND TRADEMARK OFFICE
CERTIFICATE OF CORRECTION

PATENT NO. : 4,596,820

DATED : June 24, 1986

INVENTOR(S) : Manfred Raschack et al.

It is certified that error appears in the above-identified patent and that said Letters Patent is hereby corrected as shown below:

Claim 6, line 1, "claim 6" should read "claim 5".

Claim 9, line 1, "claim 5" should read "claim 8".

Signed and Sealed this

Thirtieth Day of December, 1986

*Attest:*

DONALD J. QUIGG

*Attesting Officer*    *Commissioner of Patents and Trademarks*